United States Patent [19]

Lajoie

[11] Patent Number: 5,380,893
[45] Date of Patent: * Jan. 10, 1995

[54] HIGH PURITY FATTY ACID SALT PRODUCTS

[75] Inventor: M. Stephen Lajoie, Basking Ridge, N.J.

[73] Assignee: Church & Dwight Co., Inc., Princeton, N.J.

[*] Notice: The portion of the term of this patent subsequent to May 18, 2010 has been disclaimed.

[21] Appl. No.: 130,987

[22] Filed: Oct. 4, 1993

Related U.S. Application Data

[62] Division of Ser. No. 987,706, Dec. 9, 1992.

[51] Int. Cl.$^6$ ............................................. C07C 51/00
[52] U.S. Cl. ........................................ 554/156; 426/94; 426/807
[58] Field of Search ............... 426/74, 807; 554/156; 514/557, 558

[56] References Cited

U.S. PATENT DOCUMENTS

| | | |
|---|---|---|
| 5,212,325 | 5/1993 Lajoie | 554/156 |
| 5,236,723 | 8/1993 Lajoie | 462/72 |
| 5,250,714 | 10/1993 Lajoie | 554/156 |

*Primary Examiner*—José G. Dees
*Assistant Examiner*—Deborah D. Carr
*Attorney, Agent, or Firm*—Charles B. Barris

[57] ABSTRACT

This invention provides a high purity particulate fatty acid salt product, which is a calcium salt derivative of a fatty acid mixture such as those obtained from vegetable oil and animal tallow sources.

In a preferred embodiment, the invention fatty acid calcium salt product is substantially free of glyceride ingredient and odorant impurities, and optionally contains a flavor and aroma enhancing additive.

12 Claims, No Drawings

HIGH PURITY FATTY ACID SALT PRODUCTS

This application is a division, of application Ser. No. 07/987,706, filed Dec. 9, 1992, still pending.

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is an excellent energy source, and it is known that if the proportion of fat in cattle food is increased, lactating dairy cattle produce high milk yields without draining their reserves of body fat and without diminishing the proportion of milk fat in the milk produced.

However, it has been found that if the proportion of fat in the diet of cattle exceeds about 2% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, such later fiber digestion produces a blend of different fatty acids than that which is produced by the digestion in the rumen, and the different blend of fatty acids is less suited to the cow's metabolism.

It is known also that triglycerides and free fatty acids can physically coat fibrous or cellulosic material in the rumen and inhibit fermentation of the material by the bacteria. This has an adverse effect on the total digestibility of the diet, and can result in a reduced yield of milk and butter-fat.

There has been a continuing need for new dietary supplements for animal foodstuff which can be fed to ruminant animals without interfering with feed metabolism by rumen microorganisms.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen bypass product, and is subsequently metabolized in the abomasum or small intestine of the ruminant.

Accordingly, it is an object of this invention to provide a fatty acid salt composition which contains little or no free fatty acid or fatty acid glyceride, and which can function as a rumen bypass animal feed supplement and promote a beneficial increase in the dietary fat content of the feed.

It is another object of this invention to provide a particulate fatty acid salt product which consists essentially of calcium salts of a fatty acid mixture, and which is substantially free of glyceride ingredient and odorant impurities.

It is a further object of this invention to provide an animal feed supplement product which comprises a high purity fatty acid calcium salt ingredient, in combination with a biologically active ingredient.

Other objects and advantages of the present invention shall become apparent from the accompanying description and examples.

DESCRIPTION OF THE INVENTION

One or more objects of the present invention are accomplished by the provision of a particulate fatty acid salt product which consists essentially of the calcium salts of the following weight proportions of fatty acid constituents:

| Palmitic acid | 20–55 |
|---|---|
| Oleic acid | 25–50 |
| Linoleic acid | 2–20 |
| Stearic acid | 1–15 |
| Lauric acid | 0–10 | wherein less than about 5 weight percent of the fatty acid constituents are in glyceride form.

The fatty acid calcium salt content of an invention salt product typically is at least about 96 weight percent of the salt product weight.

The salt product is obtained by reacting a salt-forming calcium compound with a free fatty acid mixture of saturated and unsaturated carboxylic acids, such as those derived from vegetable oils and animal tallow.

Palm fatty acid distillate is a commercial product produced by distilling the fatty acids present in natural palm oil. A distillate product typically has the following weight percent content:

| Free fatty acids | 60–90 |
|---|---|
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

|  |  | preferred |
|---|---|---|
| Palmitic acid | 20–55 | 38–50 |
| Oleic acid | 25–50 | 30–40 |
| Linoleic acid | 2–20 | 5–10 |
| Stearic acid | 1–15 | 2–10 |
| Lauric acid | 0–10 | 1–5 |

Beef tallow acids are available commercially as a byproduct obtained by alkaline extraction of waste beef fat and subsequent acidification, and normally contain the following weight percent of fatty constituents:

| Free fatty acids | 60–90 |
|---|---|
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| | |
|---|---|
| Palmitic acid | 20–30 |
| Oleic acid | 35–45 |
| Linoleic acid | 2–10 |
| Stearic acid | 15–25 |

The term "glyceride" as employed herein includes fatty acid monoglycerides, diglycerides and triglycerides, and any mixture thereof.

Because unsaturated fatty acids are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid.

Illustrative of preferred additives are butylated hydroxytoluene antioxidant, and citric acid and ethylenediamine tetraacetate chelating agents. The chelating agent is added in an edible solvent such as propylene glycol to facilitate blending into the fatty acid.

An essential aspect of an invention fatty acid calcium salt product is a minimal content of fatty acid glyceride ingredient. If the fatty acid mixture component of an invention salt product originally derives from a vegetable oil or animal tallow source, it is usually necessary to employ chemical treatment to reduce the glyceride content.

A preferred fatty acid calcium salt product of the present invention is substantially free of glyceride ingredient and odorant impurities.

A fatty acid calcium salt mixture with a reduced glyceride content can be obtained by means of a process which comprises (1) forming an admixture of reactive ingredients comprising (a) a fatty acid mixture having about 5–40 weight percent of the fatty acid content in glyceride form,
(b) between about 0.8–1.2 equivalents of basic calcium metal compound per equivalent of fatty acid,
(c) a quantity of basic alkali metal compound which provides a calcium metal:alkali metal atomic ratio between about 2:1 and 10:1, and (d) between about 20–80 weight percent of an aqueous medium, based on the weight of fatty acid; and (2) recovering the salt product after completion of the exothermic salt-forming reaction; wherein the glyceride content is hydrolyzed to fatty acid and glycerol under the salt-forming conditions, and less than about 5 weight percent of the fatty acids remain in glyceride form.

A fatty acid calcium salt product of low glyceride content which is obtained by a salt-forming process of the type described above has a content of basic alkali metal compound byproduct. As illustrated in the examples, an alkali metal compound byproduct such as sodium hydroxide can be removed by slurrying the fatty acid calcium salt product in an aqueous medium at ambient temperature for a period of about 0.1–1 hour. The purified fatty acid calcium salt product can be recovered by filtration or centrifugation, and dried to a desired level of water content.

If a fatty acid calcium salt product exhibits a detectable level of unpleasant odorant impurities, the salt product can be deodorized by slurrying the product in an organic solvent such as methanol, ethanol, tetrahydrofuran, dimethylformamide, acetone, and the like.

A mixture of organic solvents can be employed, or the salt product can be slurried and recovered from successive organic solvent treatments. The purified salt product can be recovered by filtration, and dried to remove residual organic solvent. If a water-miscible organic solvent is utilized, the slurry extraction procedure can be adapted to control the amount of water remaining in the final recovered product.

In another embodiment this invention provides a particulate fatty acid salt product which consists essentially of (1) the calcium salts of the following weight proportions of fatty acid constituents:

| | |
|---|---|
| Palmitic acid | 20–55 |
| Oleic acid | 25–50 |
| Linoleic acid | 2–20 |
| Stearic acid | 1–15 |
| Lauric acid | 0–10 | wherein less than about 5 weight percent of the fatty acid constituents are in glyceride form; and (2) between about 0.05–20 weight percent of a biologically active ingredient, based on the weight of fatty acid calcium salt ingredient.

The optional biologically active ingredient of an invention fatty acid calcium salt product can be selected from a broad variety of nutrients and medicaments, either as a single component or as a mixture of components, which are illustrated by the following listing of active molecular species:

1. $C_2$–$C_{22}$ aliphatic carboxylic acids and esters, and alkali metal, ammonium and alkaline earth metal salts which are different than the selected $C_{14}$–$C_{22}$ fatty acid ingredient of the process.

2. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

| | |
|---|---|
| Protein | 12.0% |
| Fat | 0.7% |
| Lactose | 60.0% |
| Phosphorus | 0.79% |
| Calcium | 0.87% |
| Ash | 9.7% |

Another source of carbohydrate is derived from the pulp and paper industry which produces large quantities of byproduct lignin sulfonates from wood during the sulfite pulping process. The byproduct is recovered in the form of salts such as ammonium, sodium and magnesium lignin sulfonates.

3. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs thereof.

4. vitamin ingredients either singly or in combination which include thiamine HCl, riboflavin, pyridoxine HCl, niacin, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

5. Protein ingredients are obtained from sources such as dried blood or meat meal, cottonseed meal, soy meal, dehydrated alfalfa, dried and sterilized animal and poultry manure, fish meal, liquid or powdered egg, fish solubles, cell cream, rape seed oil (canola oil), and the like.

Protein equivalent ingredients include non-protein nitrogen compounds such as urea, biuret, ammonium phosphate, and the like.

6. medicament ingredients either singly or in combination which include promazine hydrochloride, chloromadionate acetate, chlorotetracycline, sulfamethazine, monensin, sodium monensin, poloxaline, and the like. Oxytetracycline is a preferred antibiotic for cattle prophylaxis.

7. enzymes such as lipolytic proteins which aid feed digestibility, e.g., by hydrolysis of fatty acid glycerides to free fatty acid and glycerol.

The biologically active ingredient quantity employed in an invention will vary in the range between about 0.05–20 weight percent, based on the weight of fatty acid calcium salt ingredient, and typically will be in the range between about 0.5–10 weight percent. The biologically active ingredient can be added during a fatty acid calcium salt-forming process. If a biologically active ingredient is heat-sensitive such as methionine, it can be blended with the final fatty acid salt product after it is recovered from the process.

It is preferred that an invention fatty acid calcium salt dietary supplement product has little or no detectable unpleasant odor. Optionally, an odor-modifying compound can be added to the product to mask any residual odor.

It is advantageous to include one or more additives which impart improved flavor and aroma to an invention fatty acid calcium salt product. Flavorant additive can be categorized as natural, artificial and WONF (with other natural flavorants), and can be added in a quantity between 0.0001–2 weight percent, based on the weight of fatty acid calcium salt ingredient.

Suitable flavorant additives which exhibit flavor and aroma enhancing organoleptic properties generally are organic compounds which correspond to structure classifications such as aliphatic and aromatic alcohols, furan ethers, thiazole alcohols, pyridine ethers and alcohols, benzofuran carbonyl compounds, aliphatic and aromatic ketones, α-diketones, pyrrole-α-diketones, aromatic sulfur compounds, phenols and phenol ethers, and the like, as recited in U.S. Pat. No. 3,702,253.

Flavorant additives are illustrated by compounds such as anethole, benzaldehyde, bergamot oil, acetoin, carvol, cinnamaldehyde, citral, ethylvanillin, vanillin, thymol, methyl salicylate, coumarin, anise, cinnamon, ginger, clove, lemon oil, 1-undecanol, 5-dodecalactone, eugenol, geraniol, geranyl acetate, guaiacol, limonene, linalool, piperonal, 2-acetyl-5-methylpyrazine, 2-ethyl-3-methoxypyrazine, 5-methylquinoxaline, 2-methyl-6-propylpyrazine, 2-methylbenzofuran, 2,2'-dithienylmethane, benzyl hexyl carbinol, furfuryl phenyl ether, difurfuryl ether, benzofuran-2-aldehyde, benzothiophene-2-aldehyde, 1-butylpyrrole-2-aldehyde, methyl decyl ketone, dipropyl ketone, ethyl benzyl ketone, 2,6-diacetylpyridine, heptane-3,4-dione, methyl thiophene-2-carboxylate, 2-hydroxyacetophenone, 4-ethyl-2-methoxyphenol, 2-oxobutan-1-ol, and the like.

The following Examples are further illustrative of the present invention. The components and specific ingredients are presented as being typical, and various modifications can be derived in view of the foregoing disclosure within the scope of the invention.

EXAMPLE I

This Example illustrates the production of fatty acid calcium salt in a batch reaction medium in accordance with the present invention.

A batch reaction is conducted for the preparation of palm oil distillate calcium salt. The palm oil distillate is the same as described in Example II.

Calcium oxide (182 g, 3.25 M) and palm oil distillate (1700 g, 6.5 M) are added to a 10% by weight solution of sodium carbonate (700 g) with stirring, and the admixture then is allowed to stand.

After a short induction period, an exothermic reaction commences and steam and carbon dioxide evolve from the semi-liquid reaction mass. The time period to solid formation is about 15 minutes. The calcium salt product is substantially free of glyceride ingredient.

A 100 g sample of fatty acid calcium salt is slurried in an aqueous medium (600 mL), and stirred for a 20 minute period to extract water-soluble sodium compounds. The extracted calcium salt product is recovered by filtration, and then slurried in 50/50 methanol/tetrahydrofuran (500 mL) for a five minute period with stirring. The solids are recovered, and dried at 60° C.

The purified product has a fatty acid calcium salt content of about 96 weight percent, a water content of about 2.0 weight percent, and is free of detectable unpleasant odor.

EXAMPLE II

This Example illustrates the continuous production of fatty acid calcium salt with a reduced content of glyceride in accordance with the present invention.

The fatty acid component is a palm fatty acid distillate of the following composition:

| | |
|---|---|
| Lauric acid | 2.3% |
| Palmitic acid | 49.9% |
| Stearic acid | 5.4% |
| Oleic acid | 35.0% |
| Linoleic acid | 7.4% |

About 15 weight percent of the fatty acid is in the form of glyceride ester.

The alkali metal component is introduced as an aqueous potassium carbonate solution. The concentration of the aqueous potassium carbonate solution is calculated to provide the required volume of water to the reaction medium, and provide potassium ions to satisfy a calcium:potassium atomic ratio of about 5:1.

The process is operated continuously with equipment which is essentially the same as described and illustrated with reference to FIG. 1 of U.S. Pat. No. 4,826,694 by W. McAskie.

Calcium oxide from a hopper and hot palm oil distillate (96° C.) from a supply line are mixed in predetermined proportions in a mixing pump. The aqueous potassium carbonate solution is added to the reactant admixture via a supply line, at a rate which provides a proportional amount of aqueous solution which is about 40 weight percent based on the total weight of fatty acid ingredient.

The hydrated mixture is passed through a mixing pump and the resultant semi-liquid reaction medium at about 100° C. is discharged as a spread layer onto a continuously moving conveyor belt. Steam and carbon dioxide evolve from the conveyor transported reaction mass.

At the end of the conveyor belt solid lumps of reaction product fall through a sizing machine onto a second conveyor belt. In this conveying zone the salt-forming reaction and evolution of water proceed to completion. The essentially dry fatty acid calcium salt product is passed through a sifter, and collected.

The residence time on the first conveyor is about 45 minutes, and the overall production time from reactant mixing to collection of the dry granulated product is about 3 hours.

The final product has a total fatty acid calcium salt content of 85 weight percent, a water content of about 7.0 weight percent, and a glyceride content of about 1.0 weight percent.

The product has a content of basic potassium metal compound. The potassium compound is removed by slurrying the fatty acid calcium salt (100 g) in an aqueous medium (600 mL) for a period of 30 minutes. The extracted product is recovered by filtration, and dried to a water content of about 3.0 weight percent.

Similar results as obtained when oxytetracycline is incorporated as an ingredient in the processing medium.

The invention fatty acid calcium salt product can be incorporated as a dietary supplement in cattle feed such as hay silage or corn silage, in a calculated quantity which will provide each animal about 300 grams per day of fatty acid salt.

What is claimed is:

1. A fatty acid salt product in dry granular form which consists essentially of the calcium salts of the following weight proportions of fatty acid constituents:

| | |
|---|---|
| palmitic acid | 20-55 |
| oleic acid | 25-50 |
| linoleic acid | 2-20 |
| stearic acid | 1-15 |
| lauric acid | 0-10 | wherein less than about 5 weight percent of the fatty acid constituents are in glyceride form.

2. A product in accordance with claim 1 which is substantially free of glyceride ingredient.

3. A product in accordance with claim 1 which is substantially free of odorant impurities.

4. A product in accordance with claim 1 which has a fatty acid calcium salt content of at least about 96 weight percent.

5. A product in accordance with claim 1 which contains an organoleptic flavorant additive.

6. A fatty acid salt product in dry granular form which consists essentially of (1) the calcium salts of the following weight proportions of fatty acid constituents:

| | |
|---|---|
| palmitic acid | 20-55 |
| oleic acid | 25-50 |
| linoleic acid | 2-20 |
| stearic acid | 1-15 |
| lauric acid | 0-10 | wherein less than about 5 weight percent of the fatty acid constituents are in glyceride form; and (2) between about 0.05-20 weight percent of a biologically active ingredient, based on the weight of fatty acid calcium salt ingredient.

7. A product in accordance with claim 6 wherein the biologically active ingredient is a nutrient.

8. A product in accordance with claim 6 wherein the biologically active ingredient is a medicament.

9. A product in accordance with claim 6 wherein the biologically active ingredient comprises at least one aminoacid.

10. A product in accordance with claim 6 wherein the biologically active ingredient comprises at least one polypeptide.

11. A product in accordance with claim 6 wherein the biologically active ingredient comprises at least one antibiotic.

12. A product in accordance with claim 6 which contains an organoleptic flavorant additive.

* * * * *